US009865368B1

(12) United States Patent
Akrotirianakis et al.

(10) Patent No.: US 9,865,368 B1
(45) Date of Patent: Jan. 9, 2018

(54) PRODUCTION OF RADIOPHARMACEUTICALS

(71) Applicant: Siemens Medical Solutions USA, Inc., Malvern, PA (US)

(72) Inventors: Ioannis Akrotirianakis, Princeton, NJ (US); Amit Chakraborty, East Windsor, NJ (US); Todd Putvinski, Morrisville, PA (US); Eric Greaser, Knoxville, TN (US); Steven Zigler, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/455,618

(22) Filed: Mar. 10, 2017

(51) Int. Cl.
*G21G 1/00* (2006.01)
*A61B 6/00* (2006.01)

(52) U.S. Cl.
CPC .......... *G21G 1/001* (2013.01); *A61B 6/4057* (2013.01); *G21G 2001/0015* (2013.01)

(58) Field of Classification Search
CPC .......... G21G 1/001; G21G 2001/0015; A61B 6/4057
USPC .......................................... 250/492.1–492.3
See application file for complete search history.

(56) References Cited

U.S. PATENT DOCUMENTS

| | | | | |
|---|---|---|---|---|
| 7,718,436 | B2 | 5/2010 | Zigler et al. | |
| 8,654,311 | B2 | 2/2014 | Lahiri et al. | |
| 8,775,136 | B2 | 7/2014 | Akrotirianakis et al. | |
| 8,977,524 | B2 | 3/2015 | Legbedji et al. | |
| 2008/0122390 | A1 | 5/2008 | Lidestri | |
| 2013/0102772 | A1* | 4/2013 | Eshima .................... | G21G 1/10 536/28.2 |

* cited by examiner

*Primary Examiner* — Michael Maskell

(57) ABSTRACT

A computer-implemented method for determining optimized amount of radiopharmaceutical to be produced at a production facility, the radiopharmaceutical being for use in nuclear imaging at customer sites, in order to meet aggregate demands of orders placed by the customer sites (e.g. medical imaging centers, hospitals, etc.), wherein the quantity of radiopharmaceutical is sufficient to meet the aggregate demand while minimizing any overproduction of the radiopharmaceutical.

9 Claims, 3 Drawing Sheets

PRODUCTION OF RADIOPHARMACEUTICALS

FIELD

This disclosure relates in general to the production of short-lived radiopharmaceuticals for positron emission tomography.

BACKGROUND

Radiopharmaceuticals such as fludeoxyglucose (FDG) used in nuclear medical imaging such as positron emission tomography (PET) are produced in cyclotrons, from bombardment of a target material with charged particles. A cyclotron is a particle accelerator that comprises two metal D-shaped electrodes placed in a vacuum chamber between two poles of a large magnet. Typically, negatively charged particles (anions) are injected into the center of the chamber via a high voltage ion source. A high frequency alternating voltage applied between the two electrodes dramatically increases the kinetic energy of the particles and the strong magnetic field forces them to travel in a spiral pathway as a beam from the center towards the perimeter of the vacuum chamber where the beam interacts with a stripping foil. The interaction results in the removal of electrons from the accelerated particles, transforming them into positively charged particles. The positive charge of the particles alters the pathway of the accelerated beam, which exits the vacuum chamber and collides with the content of the target yielding positron emitting radionuclides. For the production of fluorine-18, the accelerated particles are usually hydrogen (protium) and the target material is oxygen-18, typically in the form of enriched water. This process is called bombardment and the longer it lasts the more fluorine-18 is produced which in turn will be used to synthesize larger quantities of FDG.

Due to their unstable nature, fluorine-18 radionuclides undergo radioactive decay immediately after they are created in the bombardment process stage causing the quantity of radioactivity due to fluorine-18 to decrease. The length of time for the radioactivity to reach half of the initial amount is called half-life and for fluorine-18 it is 109.771 minutes. This relatively long half-life makes fluorine-18 an ideal radionuclide for medical imaging for two main reasons: (a) it can be transported to a substantial distance from the production facility, a radiopharmacy, and (b) after about 10 hours it is substantially eliminated from the patient's body.

A fundamental practice in every radiopharmacy is the creation of a daily schedule for the production of FDG in batches and the dispensing of the FDG into corresponding patient doses. An individual batch may provide sufficient radioactivity for up to forty or more individual doses for injecting into a patient. The number of doses that can be served by a batch depends on the distance between the radiopharmacy and the customers, nuclear imaging centers or hospitals, as well as the actual injection time of each dose. The farther a customer is from the radiopharmacy, the more radioactivity needs to be produced and therefore the bombardment process within the cyclotron needs to last longer. It is therefore important to accurately determine the amount of radioactivity that needs to be produced in order to meet the demand for the FDG for a large number of geographically dispersed customers.

Currently, in most radiopharmacies, the daily schedule for production of FDG is manually generated by radiopharmacists. Although radiopharmacists have great domain knowledge and experience, the manual generation of the schedule is a time-consuming process and may result in sub-optimal production schedules that either produce too much fluorine-18 than necessary or insufficient amount of fluorine-18. This results in excess labor costs and wasting the excessive amount of radioactivity which wastes resources and increases the production cost or not being able to completely meet the demand placed by medical imaging centers and/or hospitals. Thus, there is a need for an improved method of generating the production schedule for radiopharmaceuticals such as FDG so that FDG is produced in sufficient quantity to meet the demand without producing too much excess so that waste is minimized.

SUMMARY

According to an aspect of the present disclosure, a computer-implemented method for determining the optimized amount of radiopharmaceutical to be produced at a production facility is disclosed. The radiopharmaceutical is for use in nuclear imaging at customer sites such as medical imaging centers or hospitals. The optimized amount of radiopharmaceutical will meet the aggregate demand of orders placed by the customer sites, where the quantity of radiopharmaceutical is sufficient to meet the aggregate demand while minimizing any overproduction of the radiopharmaceutical.

According to some embodiments, a computer-implemented method for producing an optimized amount of radiopharmaceutical for preparation of doses for use in nuclear imaging at customer sites is disclosed. The optimized amount of radiopharmaceutical will meet the aggregate demands of orders placed by the customer sites while minimizing any overproduction of the radiopharmaceutical. The radiopharmaceutical is produced at a production facility operating one or more cyclotrons. According to some embodiments, a control system for controlling the operation of such radiopharmaceutical production facility is also disclosed.

BRIEF DESCRIPTION OF THE DRAWINGS

All drawing figures are schematic and are not necessarily to scale.

DETAILED DESCRIPTION

This description of the exemplary embodiments is intended to be read in connection with the accompanying drawings, which are to be considered part of the entire written description. According to an aspect of the present disclosure, a system and method of automatically determining the optimized production schedule for radiopharmaceuticals is disclosed.

First, the inventors have developed a flexible optimization model that integrates the main decisions involved in the production process of FDG. The optimization model takes into account constraints related to the bombardment and decay processes of radionuclides, the binary decisions involved in the selection of the number of cyclotrons and targets that are needed in order to produce the right amount of radioactivity that meets the demand for FDG. The production schedule planning horizon spans one day and it may be divided into a number of time periods. The demand of each imaging center is known in advance but it may vary for different time periods. The optimal solution involves four major decisions: (a) the length of the bombardment time, (b) the number of cyclotrons and targets to be used to produce enough radioactivity, and (c) the amount of radioactivity that needs to be produced in order to satisfy the total demand in each time period.

Figure 1:
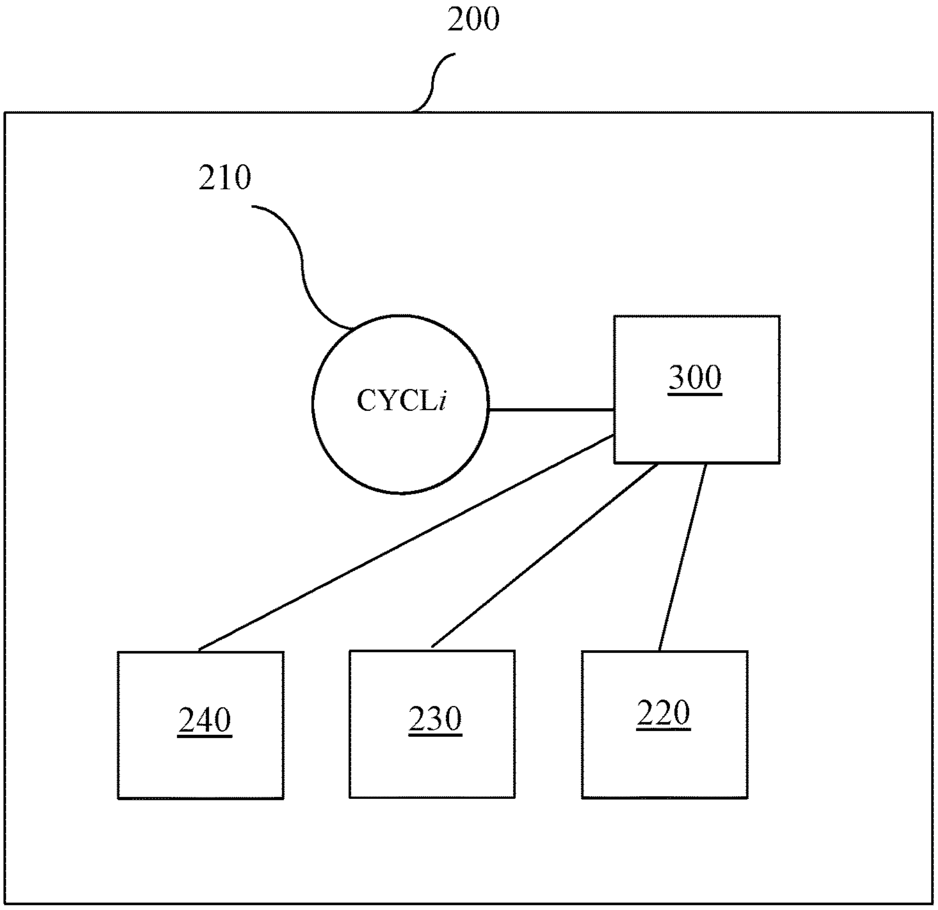
FIG. 1 is a schematic diagram of a radiopharmaceutical production facility.
Figure 2:
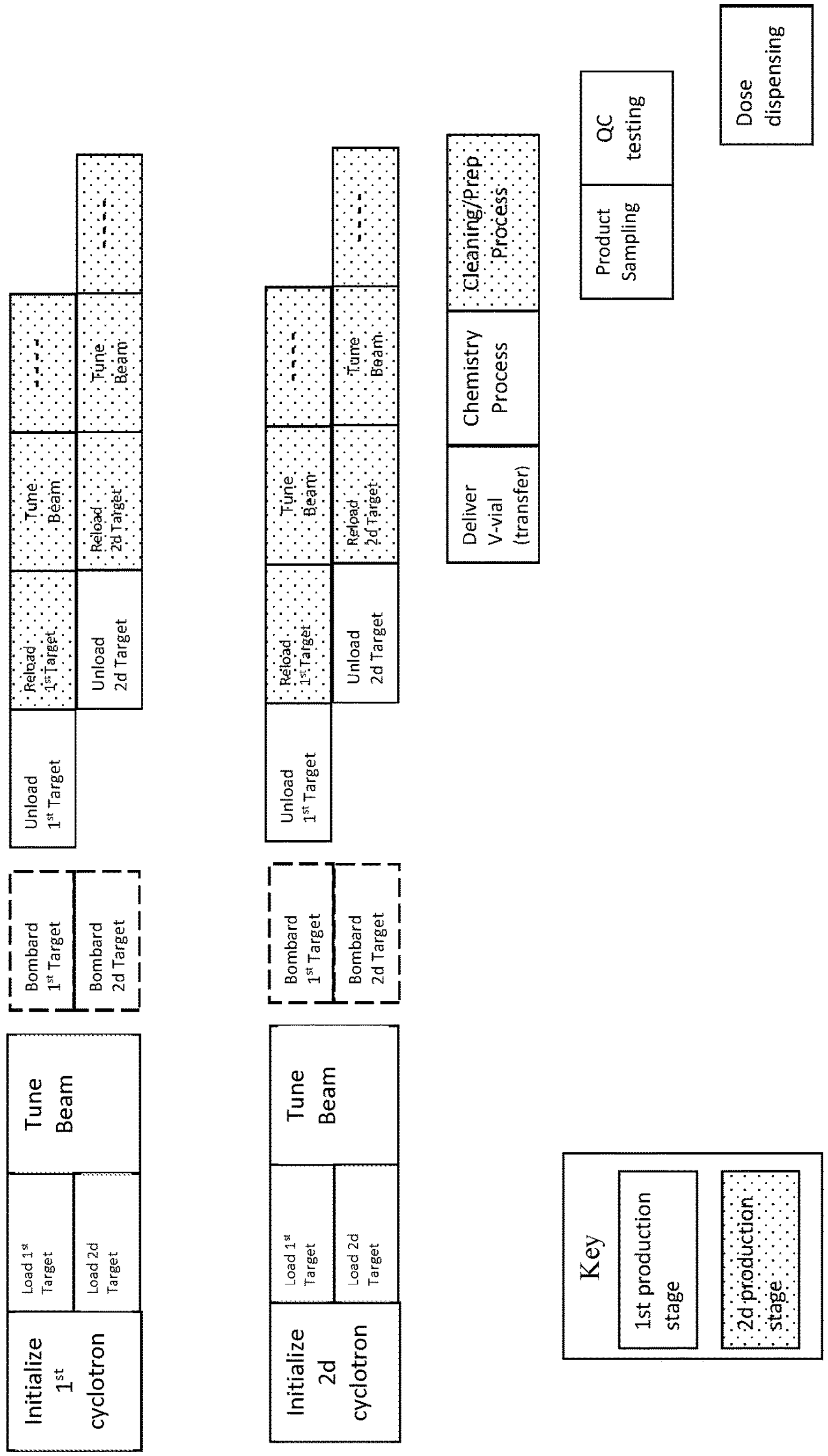
FIG. 2 is a schematic illustration of the workflow for radiopharmaceutical production process.

In general, the production of radiopharmaceutical such as FDG requires the use of complex equipment. An example of a radiopharmaceutical production facility 200 is schematically illustrated in FIG. 1. The radiopharmaceutical production facility 200 comprises: one or more cyclotrons 210 for producing fluorine-18; one or more radiopharmaceutical synthesizers 220; an analytical laboratory 230 where all the quality assurance tests are performed (e.g., testing batches for sterility, chemical purity, heavy metal contamination, etc.), and a dispenser 240 which is responsible for separating the total quantity of FDG into the unit doses which in turn will be delivered to imaging centers. The cyclotrons 210 is denoted in FIG. 1 as CYCLi where i denotes the number of cyclotrons. The operation of these components of the production facility 200 is enabled by a computer system 300. An overview of a typical work flow for the production of FDG can be seen in FIG. 2. The process has many stages. The completion time of each stage is known in advance, except from the bombardment stage (denoted by the dashed box). The time needed during the bombardment stage is determined by the optimization model defined below. The production workflow in FIG. 2 is for an example with two cyclotrons each employing two targets.

Radioactive Decay—A brief overview of radioactive decay will be discussed as a background to provide the context for the reason why scheduling and planning production of radionuclides for production of radiopharmaceutical results in much inefficiency in the currently practiced manual methods of scheduling radiopharmaceutical production.

Radionuclides have unstable nuclei that do not have enough binding energy to hold the nucleus together due to an excess of either protons or neutrons. In the process of becoming stable, radionuclides release energy and/or matter from the nucleus and often transform into a new element. Radioactive decay is a stochastic process and as such we can only determine the probability of when an individual radionuclide decays. However, for a group of radionuclides we can determine the decay rate as a whole. The half-life (denoted by $t_{1/2}$) of a group of radionuclides is the time after which, on average, half of them will have decayed and the activity of the group will be half of its initial level. The mean lifetime (denoted by $\tau$) of a radioisotope is the average time before it decays. The decay constant (denoted by $\lambda$) is the inverse of the mean lifetime (i.e., $\lambda=1/\tau$) and expresses the probability that a nucleus will undergo a transition in a specific time period. The relation between half-life and decay constant is described by expression (1)

$$t_{1/2} = \frac{\ln(2)}{\lambda} \tag{1}$$

Recalling that the half-life of fluorine 18 is 109.771 minutes and using (1) we can determine the value of its decay constant which is $\lambda_F=0.006311$ per minute.

For a given sample of a particular radioisotope, the number of decay events, denoted by dQ, which is expected to happen in the short time interval $dt=t_1-t_0$, is proportional to the difference in the number of atoms $dQ=Q_{t1}-Q_{t0}$, that is, $$-dQ \propto Q\,dt \tag{2}$$

where the minus sign indicates that the number of radioactive atoms decreases, that is $Q_{t0}>Q_{t1}$.

We can turn the proportionality in (2) into an equality by using the decay constant $\lambda$ as follows:

$$-dQ = \lambda Q dt \Rightarrow \frac{dQ}{Q} = \lambda dt \tag{3}$$

By integrating the above equation in the time interval $[t_0, t_1]$ we obtain $$\int_{Q_{t_0}}^{Q_{t_1}} \frac{dQ}{Q} = \lambda \int_{t_0}^{t_1} dt \Rightarrow \ln\frac{Q_{t_1}}{Q_{t_0}} = -\lambda(t_1 - t_0) \Rightarrow Q_{t_1} = Q_{t_0} e^{-\lambda(t_1 - t_0)} \tag{4}$$

where $Q_{t0}$ and $Q_{t1}$ represent the number of radioactive nuclei at time points $t_0$ and $t_1$.

Equation (4) is known as the radioactive decay law and plays a fundamental role in the production and distribution of radiopharmaceuticals. Based on equation (4), it is possible to determine the quantity of radioactivity that is lost to radioactive decay over a time interval. If $Q_{EOB}$ is the amount of radioactivity at the end of bombardment process (the time point denoted by $T_{EOB}$) then $Q_{INJ}$ the amount of radioactivity at the injection time, $T_{INJ}$, is defined by expression (5):

$$Q_{INJ}=Q_{EOB}e^{-\lambda(T_{INJ}-T_{EOB})} \tag{5}$$

By solving equation (5) in terms of $Q_{EOB}$, we can determine how much radioactivity is need to be produced at the end of the bombardment by expression (6):

$$Q_{EOB}=Q_{INJ}e^{\lambda(T_{INJ}-T_{BOB})} \tag{6}$$

Cyclotrons and Targetry—The amount of radioactivity produced during the bombardment of a single target $Q_F$ is defined by expression (7):

$$Q_F=(BC)(EN)(SY)(1=e^{-\lambda(T_{BMB})}) \tag{7}$$

where (BC) represents the beam current (defined as the flux of the bombarding particles), (EN) represents the enrichment of water in oxygen-18, (SY) is the saturation yield coefficient which together with the term $(1-e^{-\lambda(T_{BMB})})$ define the rate of production of fluorine-18, $T_{BMB}$ is the bombardment time, defined as $T_{BMB}=T_{EOB}-T_{BOB}$, which is the difference between the time that signifies the End Of Bombardment and the time that signifies the Beginning Of Bombardment, and $\lambda$ is the radioactive decay constant.

The beam current may range from 10 to 80 micro Ampere (μA). The end of bombardment (EOB) occurs when the beam current is set to zero. It is important to use water enriched in oxygen-18, up to at least 85%, for the production of fluorine-18 in order to be able to produce sufficient quantities of fluorine-18. The rate of production of fluorine-18 is also affected by the fact that the resulting nuclide is also radioactive and its decay is expected to start any time after it is produced. The rates of production and decay will eventually reach an equilibrium after sufficiently long bombardment times. This can be deduced by the last term in equation (7), where we can see that in the early stages of the bombardment period (i.e., when $T_{BMB}$ is small) the rate of production is high, whereas as the bombardment time $T_{BMB}$ becomes large the $(1-e^{-\lambda(T_{BMB})})$ term approaches zero and the production rate becomes very small. The saturation yield of a target represents the theoretical maximum amount of fluorine-18 ion that may be produced by a target. The saturation yield depends on the beam energy of the cyclotron and may range from 70 to 260 mCi/μA.

Target unload process stage—The Fluoride-18 ion produced by each target is consolidated into a single product during the unload process. To accomplish this, each target is sequentially unloaded to a collection vial (known as the v-vial). Targets may not be unloaded simultaneously. The unload time may be different for each target. The time when unloading of the last target is completed is defined as the end of unload (EOU). Due to the continuous decay of fluorine-18, after the unloading of the last target is complete, the total amount of fluorine-18 is determined by expression (8):

$$Q_{EOU}=Q_{F_1}+Q_{F_2}e^{-\lambda(T_3)}+Q_{F_3}e^{-\lambda(T_3)}+Q_{F_4}e^{-\lambda(T_4)} \quad (8)$$

where $Q_{EOU}$ represents the total quantity of fluorine-18 ion, decay corrected to the EOU, $Q_{F1}$ represents the quantity of fluorine-18 at the last target unload, $Q_{F2}$, $Q_{F3}$, and $Q_{F4}$ represent the quantity of fluorine-18 at the end of earlier target unloads, and $T_2$, $T_3$, $T_4$ represent the time interval between an earlier target unload and the time when the EOU was completed, $T_{EOU}$.

Target reload process stage in preparation for another bombardment—After completing the unload process, a target may be immediately reloaded in preparation for another bombardment. The time required for the reload process is the same as the time for the original target load process. After the target is reloaded, the beam may be started on the target and the next bombardment will occur after the beam tuning process. This represents the earliest time the target is available for the next bombardment session.

Fluorine-18 ion transfer process stage—Once the target unload process is complete, the vial containing the produced fluorine-18 ion is transferred to the chemistry module. Regardless of the number of targets used, there is only one transfer process for each batch of product produced. A small percentage of the total fluorine-18 ion is lost during the transfer process. The time when the transfer process is complete is defined as the beginning of synthesis (BOS). The quantity of fluorine-18 ion at the BOS is given by expression (9):

$$Q_{BOS}=Q_{EOU}(1-n(FR))e^{-\lambda T_{TRAN}} \quad (9)$$

where $Q_{BOS}$ represents the quantity of Fluorine-18 ion at the BOS, n represents the number of targets, FR is the fractional percentage lost during the unload process, and $T_{TRAN}$ is the time interval between completing the target unload process and the BOS (i.e., $T_{TRAN}=T_{Bos}-T_{EOU}$). The fractional percentage of radioactivity lost and the transfer time is the same for all targets at a given production facility.

Chemistry process stage—After the fluorine-18 ion transfer process is complete, a chemistry module converts the available fluorine-18 ion into the PET drug of interest (in this example it is FDG). A percentage of the fluorine-18 ion is lost during the chemistry process. This percentage is referred to as the percent yield of the chemistry process. The time when the chemistry process is complete is defined as the end of synthesis (EOS). The quantity of the product at the EOS is given by expression (10):

$$Q_{EOS}=(Q_{BOS})(PY)(e^{-\lambda(T_{CHEM})}) \quad (10)$$

where $Q_{EOS}$ represents the quantity of product at the EOS, PY represents the percent yield of the chemistry process, and $T_{CHEM}$ is the time interval needed by the chemistry process which is also called as chemistry time (i.e., $T_{CHEM}=T_{BOS}-T_{EOS}$). Each PET drug product has a unique percent yield and synthesis time. The percent yield and synthesis time may vary at each production facility but remain constant for each batch of a specific product. The cost of materials and labor for the chemistry process includes the costs associated with production and quality control testing. A manufacturing facility may have one or more chemistry modules. A chemistry module may be capable of making up to four batches of product.

Product sampling and quality control stage—After the chemistry process is complete, the product is sampled for purposes of quality control (QC) testing. This sample is a percentage of the product present at the end of the chemistry process. The remaining quantity of the product is available for dose dispensing (DSP) and is given by expression (11):

$$Q_{DSP}=(1-(QS))Q_{EOS} \quad (11)$$

where $Q_{DSP}$ represents the quantity of product available for dose dispensing, and QS represents the percentage of the product used in the sample. Each PET drug has a unique sample percentage and sampling time. The sample percentage and the sampling time may vary at each production facility and are constant for each batch of product at a production facility. After the sample has been removed from the product, the QC process is performed and the dose dispensing process may begin on the remaining product, $Q_{DSP}$. Each PET drug has a unique QC process time which may vary for each production facility.

Dose dispensing stage—The dose dispensing process may be executed simultaneously with the QC process. The dispensed doses may not be released from the production facility until after the QC process is complete and the batch meets all QC release criteria. The aggregate, decay-corrected, quantity of all dispensed doses cannot exceed $Q_{DSP}$. This relationship is given by expression (12):

$$Q_{DSP} \geq \sum_{i=1}^{N_{DOSES}} (Q_{DOSE_i})\left(e^{\lambda(T_{DOSE_i})}\right) \quad (12)$$

where $Q_{DOSEi}$, represents the quantity of product in the individual dose i, and $T_{DOSEi}$, is the time interval between the injection time $T_{INJi}$ of dose i and the EOS (that is, $T_{DOSEi}=T_{INJi}-T_{EOS}$), and the summation is in terms of all doses, $N_{DOSES}$, assigned to the batch.

The radiopharmaceutical production model described above will be applied to an example in which we consider a multi-period process, where a day is divided into a small number of periods. Production that takes place in production stage t is transported to the customers, the imaging centers, in the following stage t+1. We denote by $N_{PRD}$ the number of production stages being considered in a day. Due to the nature of the problem, its complexity becomes increasingly large as the number of periods increases. Typically, there are 2 to 3 production and transportation periods in a day.

Decision variables—There are decision variables that are unknown quantities that the decision-maker can control and needs to determine their optimal values. For example, in applying the disclosed model, the number of cyclotrons and targets needed to produce enough radioactivity and satisfy all the orders for radiopharmaceuticals placed during a day is unknown. However, the decision-maker would like to know the minimum number of cyclotrons and/or targets that are needed since there are costs associated with their use. The variables associated with the production process are provided in the Definitions section below.

Production variables—The beginning and end of bombardment of target j at cyclotron i in production stage t are denoted by $BOB_{ijt}$ and $EOB_{ijt}$, respectively. The beam current applied on target j in cyclotron i at production stage t is denoted by $BC_{ijt}$. We use a binary variable $Z_{ijt}$ to express the fact that a target may be in use or not in use in a particular time period. More specifically, the binary variable $Z_{ijt}$ is equal to 1 if target j in cyclotron i during production stage t is used, otherwise $Z_{ijt}$ is 0. For example, if the second target of the first cyclotron in the first production stage is not used $Z_{121}=0$.

The latest time of the target unload process at production stage t is denoted by EOUt and the radioactivity level at that time is denoted by $Q_t^{EOU}$. The time when the dispensing of the doses at production stage t starts is denoted by $T_i^{DSP}$, and the total radioactivity at that time is denoted by $Q_t^{DSP}$.

The complete production optimization model is defined by equations (13) through (24) presented below:

In order to determine the optimized amount of radiopharmaceutical to be produced at a production facility, ($EOB_{ijt}-BOB_{ijt}$), the duration of bombardment of cyclotron i, target j, in production stage t of the production facility is minimized by the following expression (13), $$\min \sum_{i\in C} \sum_{j\in G} \sum_{t\in T} (EOB_{ijt} - BOB_{ijt})t, \qquad (13)$$

wherein $EOB_{ijt}$ is the time of the end of bombardment of cyclotron i, target j, in production stage t, and $BOB_{ijt}$ is the time of the beginning of bombardment of cyclotron i, target j, in production stage t;

subject to the following constraints, $$T_{BMB}^{min} * z_{ijt} \le EOB_{ijt} - BOB_{ijt} \le T_{BMB}^{max} * z_{ijt},\ \forall i \in C,\ \forall j \in G,\ \forall t \in T \qquad (14),$$

wherein $T_{BMB}^{min}$ is minimum bombardment time, $T_{BMB}^{max}$ is maximum bombardment time, $C=\{1, \ldots, N_{CYCL}\}$, where $N_{CYCL}$ is the number of cyclotrons available in a production facility (a radio-pharmacy), $G=\{1, \ldots, N_{TRG}\}$, where $N_{TRG}$ is the number of targets available in all cyclotrons that exist in a production facility, and $T=\{1, \ldots, N_{PRD}\}$, where $N_{PRD}$ is the number of production stages considered in the model, $$BC^{min} * z_{ijt} \le BC_{ijt} BC^{max} * z_{ijt},\ \forall i \in C,\ \forall j \in G,\ \forall t \in T \qquad (15),$$

wherein $BC^{min}$ is the lower bound on the beam current of a cyclotron, $BC_{ijt}$ is the beam current of cyclotron i, target j, in production stage t, $BC^{max}$ is the upper bound on the beam current;

$$EOB_{i1t} = EOB_{ijt},\ \forall i \in C,\ \forall j \in G,\ \forall t \in T \qquad (16),$$

wherein $EOB_{i1t}$ is the time of the end of bombardment of cyclotron i, target 1, in production stage t, wherein the constraint (16) provides that for every cyclotron, the end of the bombardment of all of the targets happen at the same time, $$EOB_{i1t} + \sum_{j\in G} z_{ijt} * T_{ij}^{UNLD} \le EOU_t,\ \forall\, i \in C,\ \forall\, t \in T, \qquad (17)$$

wherein $T_{ij}^{UNLD}$ is the unload time of target j in cyclotron i, and $EOU_t$ is the latest time of completion of all unloading process in production stage t, wherein the constraint (17) provides that at every production stage t, each target j in cyclotron i is unloaded sequentially after the end of the bombardment process, $$BOB_{ij1} = T_{INIT}\ \forall i \in C,\ \forall j \in G,\ \text{where } T_{INIT} = T_{START} + T_{CYCL-INIT} + T_{TRG-LOAD} T_{TUNE-BEAM} \qquad (18),$$

wherein $BOB_{ij1}$ defines the time of the beginning of bombardment of cyclotron i, target j, in production stage 1 (i.e. the very first production period), $T_{INIT}$ represents the total amount of time required before the bombardment begins, $T_{START}$ represents the time when the production process start (e.g., if the production process starts at 01:15 then $T_{START}=75$ (i.e., 75 minutes past midnight), $T_{CYCL-INIT}$ is the amount of time required to initialize cyclotron i, $T_{TRG-LOAD}$ is the amount time it takes to load target j, and $T_{TUNE-BEAM}$ is the amount of time required to tune cyclotron i's beam current;

$$BOB_{ijt} \ge EOU_{t-1}(+T_{PREP}),\ \forall i \in C,\ \forall j \in G,\ \forall t T-\{1\} \qquad (19),$$

wherein $EOU_{t-1}$ is the time point representing the end of unloading of target j in production stage t−1 (i.e., one previous to the production stage t), and $T_{PREP}$ is the amount of time required to prepare cyclotron i for the next production stage;

$$Q_t^{EOU} = \left[\sum_{i\in C} \sum_{j\in G} BC_{ijt} * SY_{ij} * EN_{ij} * \left(1 - e^{\lambda(EOB_{ijt} - BOB_{ijt})}\right)\right] * e^{-\lambda(EOU_t - EOB_{ijt})},\ \forall\, t \in T, \qquad (20)$$

wherein $Q_t^{EOU}$ is the total radioactivity produced at $EOU_t$, $BC_{ijt}$ is the beam current of cyclotron i, target j, in production stage t, $SY_{ij}$ is saturation yield of target j in cyclotron i, and $EN_{ij}$ is enrichment of the $O^{18}$ water by target j in cyclotron i;

$$Q_t^{DSP} = Q_t^{EOU} * (1 - FR) * PY * (1 - QS) * e^{-\lambda(T_{TRAN} + T_{CHEM} + T_{QC})},\ \forall\, t \in T, \qquad (21)$$

wherein $T_{TRAN}$ is the time required for completing the target unload process, $T_{CHEM}$ is the time required for completing the chemistry process, and $T_{QC}$ is the time required for completing the quality control test;

$$T_t^{DSP} = EOU_t + T_{TRAN} + T_{CHEM} + T_{QC},\ \forall t \in T \qquad (22),$$

wherein $T_t^{DSP}$ is the time when dose dispensing begins in production stage t;

$$Q_t^{DSP} \ge \sigma \sum_{i\in H_t} q_i * e^{-\lambda(T_{it}^{INJ} - T_t^{DSP})},\ \forall\, t \in T, \qquad (23)$$

wherein σ is a constant ≥1, $H_t=\{2, \ldots, N_{SITES}\}$, where $N_{SITES}$ is the number of customer sites that have placed orders whose demand is to be satisfied by production stage t, qi is radioactivity demand of customer (i.e., an imaging center) i, and $T_{it}^{INJ}$ is the earliest injection time of all orders placed by a customer i, in production stage t;

$$Z_{ijt} \in \{0,1\} \qquad (24)$$

For any given radio-pharmacy, the objective is to run an efficient production of radiopharmaceutical so that the production cost is minimized while meeting all of the demands of the customers, the imaging centers. In other words, producing just enough radiopharmaceuticals to meet all of the demand without over producing.

According to the present disclosure, the objective function is defined by the expression (13) which is finding the minimum production cost for a radio-pharmacy where i represents a cyclotron among the set C of cyclotrons available to the radio-pharmacy for production, j represents a target among the set G of targets available to each cyclotron, and t represents a production stage among the set T of multiple production stages in a given day. The production cost is defined as a multiple of the bombardment time needed at every stage of the production phase.

The constraints defined by inequalities in constraint (14) enforce the bombardment time of a target j in a cyclotron i to be in a specific interval, where $T_{BMB}^{min}$ and $T_{BMB}^{max}$ are the minimum and maximum allowed bombardment times, respectively. Typically, $T_{BMB}^{min}$=30 minutes and $T_{BMB}^{max}$=4 hours or 240 minutes.

Similarly, the inequalities in constraint (15) deal with the lower and upper bounds of the beam current used for the cyclotron, where $BC^{min}$ and $BC^{max}$ are the lower and upper bounds respectively. Typical values are $BC^{min}$=40 μA and $BC^{max}$=80 μA, depending on the type of the cyclotron used. The use of the binary variables $Z_{ijt}$ in both equations (14) and (15) ensure that the bombardment time and beam current are kept within acceptable intervals if a target is actually used. For the targets that are not used these intervals automatically become zero.

Constraint (16) ensure that for every cyclotron the end of the bombardment for the targets happen at the same time point. The requirement that at every production stage each target in a cyclotron is unloaded sequentially after the end of the bombardment is described by constraint (17). Note that these constraints allow the end of bombardment of different cyclotrons to take place at different points in time. The end of unload though happens in a common point in time for all available cyclotrons. On the other hand, constraint (19) models the fact that the beginning of the bombardment in stage t must happen after the dispensing time in the previous stage t−1. This constraint links the production in consecutive stages.

The constraint that defines the amount of radioactivity that has been produced at the end of unload time, in production stage t, is described in (20). Note that the first exponential term defines the total radioactivity produced during the bombardment of all available targets in all available cyclotrons. Once the bombardment of the targets has been finished the radioactive decay process starts. This decay process is modeled by the second exponential term in equation (20).

After all the targets have been unloaded, the radioactive material is transferred to the chemistry module where the synthesis process takes place in order to convert the fluorine-18 ion into a PET drug (the FDG). Following the end of synthesis, the FDG product is sampled and the quality control process starts. The radioactivity decays through all of the above three mentioned stages. The formula that measures the amount of radioactivity after the transfer, chemistry, and quality control processes have been completed is described in constraint (21). Furthermore, constraint (22) connect the time line between the EOU and the dispensing times at each stage.

Constraint (23) connects the total amount of radioactivity that must be produced at dispensing time and the total amount of radioactivity that has been ordered by the imaging centers that are going to be served during the production stage t. Here, $q_i$ is the radioactivity ordered by imaging center i and $qi{*}e^{-\lambda(T_{it}^{INJ}-T_t^{DSP})}$ is the amount we need at the dispensing step in production stage t for imaging center i. $Q_t^{DSP}$ should be more than the total radio-activity ordered at dispensing time at each stage. For this reason we multiply the total ordered radioactivity by a constant σ≥1. For example, if we want to produce 10% more radioactivity than the total ordered then we set σ=1.1.

Finally, all the variables are continuous except $Z_{ijt}$. These requirements are described by the last constraint (24) in the model.

Computational Results

To demonstrate the efficiency and practicality of the model, we initially present a case study describing the production of FDG orders during a typical day in a radio-pharmacy The model was executed by the use of FICO-Xpress optimization package, which includes a powerful modeling language (Mosel) and efficient solvers that can solve problems with integer and continuous variables as well as linear and nonlinear constraints.

For the case study, we selected a typical week day which consists of 10 medical imaging centers, denoted by C1 through C10. Those centers were requesting 47 doses in total. The day was split into two periods. Table 1 presents more details about the orders and how they are placed in the two different periods. The production site (radio-pharmacy) is denoted by C0. As can be seen in Table 1, there are customers that have ordered many doses and these are placed in different periods based on their injection time. Orders that need to be injected later in the day are placed in the second period.

TABLE 1

Details for the orders placed by imaging centers.

| Customer ID | Doses in P1 | Earliest inj. in P1 | Doses in P2 | Earliest inj P2 |
|---|---|---|---|---|
| C1 | 1 | 08:15 | 1 | 13:15 |
| C2 | 3 | 06:50 | 3 | 10:10 |
| C3 | 2 | 08:00 | 2 | 09:40 |
| C4 | 1 | 06:50 | 1 | 13:30 |
| C5 | 5 | 08:30 | — | — |
| C6 | 1 | 08:15 | 1 | 09:55 |
| C7 | 5 | 08:30 | 5 | 10:10 |
| C8 | 4 | 08:15 | — | — |
| C9 | 4 | 08:30 | 4 | 10:10 |
| C10 | 4 | 08:30 | — | — |

Table 2 summarizes the values we used for the various parameters of the production optimization model. It should be mentioned that these values can be changed by the users based on their preferences and the availability of the resources in each production facility.

TABLE 2

Initialization of the major parameters in the production process.

| Production Parameter | Value | Unit of measurement |
|---|---|---|
| $BC^{min}$ | 40 | μA |
| $BC^{max}$ | 80 | μA |

TABLE 2-continued

Initialization of the major parameters in the production process.

| Production Parameter | Value | Unit of measurement |
|---|---|---|
| EN | 85 | % |
| FR | 100 | mCi |
| $N_{CYCL}$ | 2 | — |
| $N_{TRG}$ | 2 | — |
| PY | 75 | % |
| QS | 0.07 | mL |
| $T_0^{CYCL}$ | 15 | minutes |
| $T_{BMB}^{min}$ | 15 | minutes |
| $T_{BMB}^{max}$ | 180 | minutes |
| $T_{CHEM}$ | 50 | minutes |
| $T_{LOAD}^{TRG}$ | 10 | minutes |
| $T_{QC}$ | 25 | minutes |
| $T_{TRAN}$ | 5 | minutes |
| $T_{TUNE}^{BEAM}$ | 5 | minutes |
| $T_{UNLD}$ | 7 | min/target |
| SY | 110 | mCi/μA |

Tables 3 and 4 summarize the results for the production of radioactivity during production stages 1 and 2. The production for Stage 1 started at 01:00 and once it was completed, the production for Stage 2 started. For this case study, we set the production facility to have two cyclotrons and each cyclotron being capable of using up to two targets. The model decided to use all available resources in Stage 1, meaning that both cyclotrons and all 4 targets were used to produce enough radioactivity to satisfy the demand of the imaging centers in Stage 1. The bombardment time for each of the 4 targets was 60 minutes. This means that a total of 4 radioactivity production hours was achieved in duration of 1 hour. Taking into consideration the preparation time before the start of the bombardment process (i.e., cyclotron initialization time (15 minutes), target load time (10 minutes) and beam time tuning (5 minutes)), the model determines that the beginning of the bombardment for each target should start on 01:30 and should end on 02:30. At that time, the total radioactivity produced by all targets is 9,189.47 mCi. After 02:30, the radioactive material produced will start decaying. Once the bombardment of each target is completed, the targets are unloaded. The unload process takes 2×7=14 minutes to complete, which means that the unload process will complete on 02:44 and the radioactivity at that time is 8,412.38 mCi (note the decrease in the amount of radioactivity compared to the amount at the end of bombardment due to the decay process). During the transfer and chemistry processes, the radioactivity keeps decaying and at the time of dispensing, the radioactivity has become 3,933.51 mCi, which represents a 10% increase to the total customer radioactivity demand at dispensing time is which is equal to 3,575.92 mCi.

TABLE 3

Results of the radioactivity production during Stages 1 and 2.

| Stage # | $Q_t^{EOB}$ | $Q_t^{EOU}$ | $Q_t^{EOS}$ in | $Q_t^{DSP}$ | $Q_t^{CUST}$ |
|---|---|---|---|---|---|
| 1 | 9189.47 | 8412.38 | 4952.43 | 3933.51 | 3575.92 |
| 2 | 3614.2 | 3458.01 | 2035.76 | 1616.92 | 1469.92 |

After all the targets have been unloaded, production of the radioactivity needed to satisfy the demand of Stage 2 can start. Once we take into account the 30 minutes preparation time preceding a bombardment, the beginning of bombardment in Stage 2 is at 03:14. This time the model decided to use on one target to cover the demand for Stage 2. The bombardment time was between 03:16 (we assumed a 2 minute gap between each production stage) and 05:40. In other words, by bombarding a single target for 144 minutes (or 2 hours and 24 minutes) it suffices to produce the necessary amount of radioactivity and meet the demand for FDG of every imaging center. Note that the demand of FDG in Stage 2 is less than that of Stage 1, and therefore the use of only one target is justified. The radioactivity at the end of bombardment is 3,614.2 mCi, which is substantially smaller than the corresponding radioactivity produced in Stage 1. This may be attributed to the following factors: (a) the customers (the imaging centers) in Stage 2 are closer to the radio-pharmacy, (b) the injection times are closer to the beginning of the bombardment in Stage 2, and (c) there are fewer customers and their demand of FDG is smaller. At the end of the unload of the single target the radioactivity has been decreased to 3,458.01 mCi and 1,616.92 mCi, respectively. The total customer radioactivity demand at dispensing time is 1,469.92 mCi.

TABLE 4

Results of the different production times during Stages 1 and 2

| Stage # | $T_t^{EOB}$ | $T_t^{EOU}$ | $T_t^{EOS}$ | $T_t^{DSP}$ |
|---|---|---|---|---|
| 1 | 02:30 | 02:44 | 04:00 | 04:00 |
| 2 | 05:40 | 05:47 | 07:07 | 07:07 |

(Note:
We assume that the EOS coincides with the dispensing time.)

Definitions

I. Index sets appearing in this disclosure:

C={1, . . . , $N_{CYCL}$}, where $N_{CYCL}$ is the number of cyclotrons available in a production facility (a radio-pharmacy);

T={1, . . . , $N_{PRD}$}, where $N_{PRD}$ is the number of production stages considered in the model;

G={1, . . . , $N_{TRG}$}, where $N_{TRG}$ is the number of targets available in all cyclotrons that exist in a production facility; and $H_t$={2, . . . , $N_{SITES}$}, where $N_{SITES}$ is the number of all customer sites (i.e., imaging centers, hospitals, etc.).

II. Parameters:

$BC^{min}$: lower bound on the beam current of a cyclotron;

$BC^{max}$: upper bound on the beam current;

EN: enrichment of the $O^{18}$ water;

FR: percentage of radioactivity lost during the unload process;

PY: percent yield of the radioactivity of an unloading process;

qi: radioactivity demand of customer (imaging center) i;

QS: percentage of product used as the sample testing during Quality Control testing;

SY: saturation yield;

$T_0^{CYCL}$: initialization time for each cyclotron;

$T_{BMB}^{min}$: minimum bombardment time;

$T_{BMB}^{max}$: maximum bombardment time;

$T_{CHEM}$: time required for the chemistry process;

$T_i^{INJ}$: the earliest injection time of all orders placed by a customer i;

$T_{PREP}$: the amount of time needed to prepare the cyclotron for the next time period;

$T_{START}$: the time when the whole production process starts;

$T_{CYCL-INIT}$: time it takes to initialize a cyclotron;

$T_{TRG-LOAD}$: time it takes to load the targets;

$T_{TUNE-BEAM}$: time it takes to tune the cyclotron's beam current;

$T_{QC}$: time required completing the quality control test;

$T_{TRAN}$: time required for completing the target unload process;

$T_{UNLD}$: unload time of each target in each cyclotron; and

λ: the radiation decay rate of the radiopharmaceutical (for FDG, the value is 0.006311).

III. Continuous Decision Variables $BC_{ijt}$: beam current of cyclotron i, target j, in production stage t;

$BOB_{ijt}$: the time of the beginning of bombardment of cyclotron i, target j, in production stage t;

$EOB_{ijt}$: the time of the end of bombardment of cyclotron i, target j, in production stage t;

$EOU_t$: the time point representing the end of the target unloading process in production stage t;

$EOU_{t-1}$: the time point representing the end of the target unloading process in the production stage one previous to the production stage t;

$Q_t^{EOU}$: the total radioactivity produced at $EOU_t$;

$T_t^{DSP}$: beginning time of distribution in production stage t;

$Q_t^{DSP}$: the total radioactivity produced at $T_t^{DSP}$;

IV: Binary Decision Variable $Z_{ijt}$: indicates whether cyclotron i and target j are in use in production stage t, $Z_{ijt}$=1 if in use, $Z_{ijt}$=0 if not in use.

According to some embodiments of the present disclosure, a computer-implemented method for determining optimized amount of radiopharmaceutical to be produced at a production facility is disclosed. The radiopharmaceutical is for use in nuclear imaging at customer sites, in order to meet the aggregate demand of the orders placed by the customer sites. The production facility is operating one or more cyclotrons.

Figure 3:
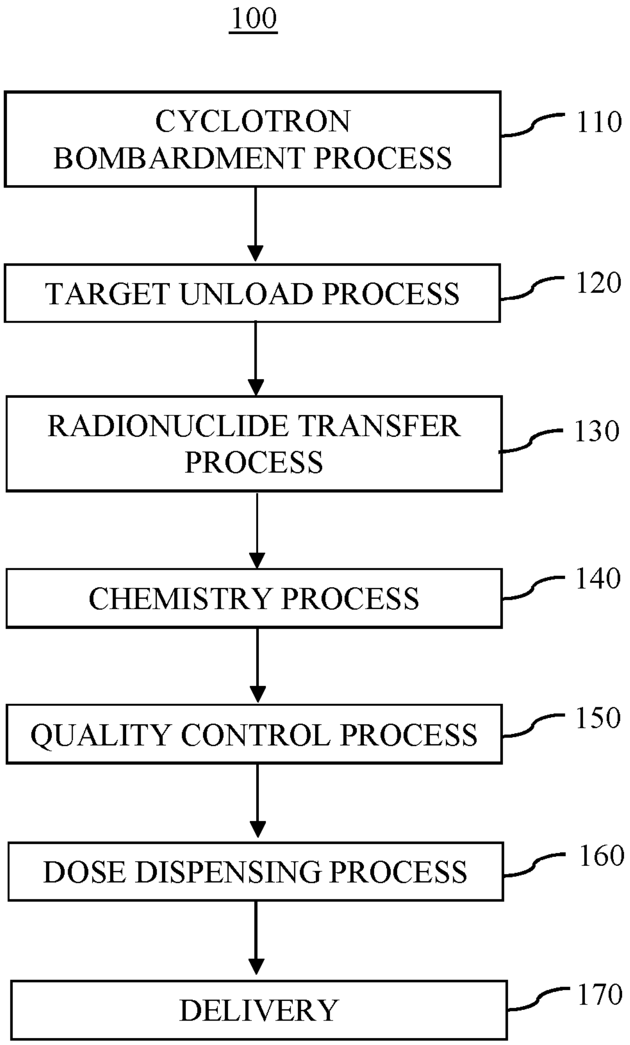
FIG. 3 is a flowchart outline of the disclosed radiopharmaceutical production process.

Referring to the flow chart 100 shown in FIG. 3, the production of radiopharmaceutical comprises: a cyclotron bombardment process 110 during which a target material (a radionuclide precursor) is bombarded with charged particles to produce radionuclide material; a target unload process 120; a radionuclide transfer process 130 during which the radionuclide material is transferred from the target unload process to a chemistry process module; a chemistry process 140 during which the radionuclide material is converted in to a radiopharmaceutical; a quality control process 150 during which the radiopharmaceutical is sampled for quality control testing; a dose dispensing process 160 during which the radiopharmaceutical is dispensed into individual doses; and delivery 170 to the customer sites.

Referring to FIG. 1, the computer system 300 that controls the operation of the radiopharmaceutical production facility 200 also executes the methods disclosed herein. The computer system 300 executes the process of determining the optimized amount of radiopharmaceutical to be produced at the production facility. The computer system also controls the operation of the production facility. The method for determining optimized amount of radiopharmaceutical to be produced at a production facility is performed by the computer system 300 and comprises:

determining the total amount of radionuclide $Q_t^{DSP}$ that is desired to be produced by $N_{CYCL}$ number of cyclotrons and $N_{TRG}$ number of targets in the production facility at the end of dose dispensing process in production stage t, (where t=1 to $N_{PRD}$), wherein $Q_t^{DSP}$is sufficient to meet the aggregate amount of radiopharmaceuticals $Q^{CUST}$ ordered by the customer sites while minimizing any overproduction of the radionuclide, whereby $Q_t^{DSP}$ meets the conditional constraint (23) defined above, wherein the $Q_t^{DSP}$ is determined by solving the constraint (21) defined above, wherein $Q_t^{EOU}$ is determined by solving the expression (20) defined above, wherein ($EOB_{ijt}$−$BOB_{ijt}$), the duration of bombardment of cyclotron i, target j, in production stage t, is minimized by the expression (13) subject to the constraints (14) through (19) presented above, where the constraint (19) provides that the beginning of the bombardment in production stage t must happen after the dispensing process in the previous stage t−1.

The FDG production model represented by the expression (13) is a large-scale nonlinear optimization with integer and continuous variables and as such the computer system 300 that controls the operation of the radiopharmaceutical production facility 200 to produce the optimal solution would have sufficient computing power to carry out the computations necessary for the model. As the number of orders for FDG increases the number of time periods that divide the production day will increase too. As a result the number of constraints and (binary and continuous) variables will increase accordingly. In order to determine the optimal solution of such an optimization problem the computer system 300 preferably is a powerful computer having one or more processors providing the computing power. In some embodiments, the computer system 300 can be parallel computers with the commuting time decreasing as the number of computers devoted to solve the optimization model increases. The input to the computer system 300 will be the order details provided by the imaging centers (e.g., the amount of radioactivity at the injection time, the time when the FDG dose will be injected in the patients body, the number of cyclotrons and targets that are available in the production facility, etc). The output of the computer will be the total amount of FDG needed to satisfy the demand for each period during a specific day. Also, for each time period, the computer system will provide the time when the FDG will be ready for dispensing and transported to the imaging centers or hospitals.

In some embodiments of the method for determining optimized amount of radiopharmaceutical to be produced at a production facility, $T_{BMB}^{min}$=30 minutes and $T_{BMB}^{max}$=4 hours or 240 minutes. In some embodiments of the method, $BC^{min}$=40 μA and $BC^{max}$=80 μA.

According to some embodiments, a computer-implemented method for producing an optimized amount of radiopharmaceutical for preparation of doses for use in nuclear imaging at customer sites in order to meet the aggregate demands of the orders placed by the customer sites is disclosed. The radiopharmaceutical is produced at the production facility operating $N_{CYCL}$ number of cyclotrons and $N_{TRD}$ number of targets. The production of radiopharmaceutical comprises the steps illustrated in the flowchart shown in FIG. 3. According to an aspect of the present disclosure, the method for producing the optimized amount of the radiopharmaceutical performed by a computerized production facility comprises the steps of:

determining the total amount of radionuclide $Q_t^{DSP}$ that is desired to be produced by $N_{CYCL}$ number of cyclotrons and $N_{TRG}$ number of targets in the production facility at the end of dose dispensing process in production stage t, (where t=1 to $N_{PRD}$), wherein $Q_t^{DSP}$ is sufficient to meet the aggregate amount of radiopharmaceuticals $Q^{CUST}$ ordered by the customer sites while minimizing any overproduction of the radionuclide, whereby $Q_T^{DSP}$ meets the conditional constraint (23) defined above, wherein the $Q_t^{DSP}$ is determined by solving the expression (21) defined above, wherein $Q_t^{EOU}$ is total amount of radionuclides produced at the end of target unloading process of the one or more cyclotrons in production stage t, and is determined by solving the expression (20) defined above, wherein the variables are as defined above, and wherein $(EOB_{ijt}-BOB_{ijt})$, the duration of bombardment for cyclotron i, target j, in production stage t is minimized by the expression (13) defined above, subject to the constraints (14) through (19) defined above, where the constraint (19) provides that the beginning of the bombardment in production stage t must happen after the dispensing process in the previous stage t−1; and operating each of the cyclotron i with target j in a production stage t so that the cyclotron's bombardment process begins at time $BOB_{ijt}$ and ends at time $EOB_{ijt}$ to produce an appropriate amount of radionuclide to produce the determined amount $Q_t^{DSP}$ of radiopharmaceutical at the end of dose dispensing process according to the constraints (14)-(19).

In some embodiments of the method for producing optimized amount of radiopharmaceutical, $T_{BMB}^{min}$=30 minutes and $T_{BMB}^{max}$=4 hours or 240 minutes. In some embodiments of the method for producing optimized amount of radiopharmaceutical, $BC^{min}$=4 μA and $BC^{max}$=80 μA.

According to some embodiments, a control system for controlling the operation of a radiopharmaceutical production facility is disclosed where the radiopharmaceutical being for use in nuclear imaging at customer sites, in order to meet aggregate demands of orders placed by the customer sites, wherein the production facility is operating one or more cyclotrons, wherein the production of radiopharmaceutical comprises: a cyclotron bombardment process stage during which a target radionuclide precursor material is bombarded with charged particles to produce a radionuclide material; a target unload process stage; a radionuclide transfer process stage during which the radionuclide material is transferred from the target unload process stage to a chemistry process stage, wherein during the chemistry process stage the radionuclide material is converted in to a radiopharmaceutical; a quality control process stage during which the radiopharmaceutical is sampled for quality control testing; a dose dispensing process stage during which the radiopharmaceutical is dispensed into individual doses for delivery to the customer sites. An example of such control system is the computer system 300 of FIG. 1. The control system can comprise: a processor having a non-transitory machine-readable storage medium encoded with computer program code, wherein when the processor executes the computer program code, the processor performs the computer-implemented method for determining optimized amount of radiopharmaceutical to be produced by the production facility described above.

The description of the embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method for determining optimized amount of a radiopharmaceutical to be produced at a production facility, the radiopharmaceutical being for use in nuclear imaging at customer sites, in order to meet aggregate demands of orders placed by the customer sites, wherein the production facility is operating one or more cyclotrons, wherein the production of the radiopharmaceutical comprises: a cyclotron bombardment process stage during which a target radionuclide precursor material is bombarded with charged particles to produce a radionuclide material; a target unload process stage; a radionuclide transfer process stage during which the radionuclide material is transferred from the target unload process stage to a chemistry process stage, wherein during the chemistry process stage the radionuclide material is converted in to a radiopharmaceutical; a quality control process stage during which the radiopharmaceutical is sampled for quality control testing; a dose dispensing process stage during which the radiopharmaceutical is dispensed into individual doses for delivery to the customer sites, the method being performed by the computer and comprising:

determining the total amount of radionuclide $Q_t^{DSP}$ that is desired to be produced by $N_{CYCL}$ number of cyclotrons and $N_{TRG}$ number of targets in the production facility at the end of dose dispensing process in production stage t, (where t=1 to $N_{PRD}$), wherein $Q_t^{DSP}$ is sufficient to meet the aggregate amount of radiopharmaceuticals $Q^{CUST}$ ordered by the customer sites while minimizing any overproduction of the radionuclide, whereby $Q_t^{DSP}$ meets the following conditional constraint (23):

$$Q_t^{DSP} \geq \sigma \sum_{i \in H_t} q_i * e^{-\lambda(T_{it}^{INJ} - T_t^{DSP})}, \ \forall \, t \in T \tag{23}$$

wherein σ is ≥1, $q_1$ is the total radioactivity demand of customer site i that has placed one or more orders, wherein $H_t=\{2, \ldots, N_{SITES}\}$, where $N_{SITES}$ is the number of customer sites that have placed orders whose demand is to be satisfied by production stage t, wherein λ is radioactivity decay rate of the radionuclide, wherein $T_{it}^{INJ}$ is the time for the earliest order for radiopharmaceutical among the one or more orders placed by customer site i whose demand is to be satisfied by production stage t, wherein $T_t^{DSP}$ is the time when the dose dispensing process begins in production stage t, and is defined by the following expression (22):

$$T_t^{DSP}=EOU_t+T_{TRAN}+T_{CHEM}+T_{OC}, \ \forall t \in T, \tag{22}$$

wherein the $Q_t^{DSP}$ is determined by solving the following expression (21):

$$Q_t^{DSP} = Q_t^{EOU} * (1 - FR) * PY * (1 - QS) * e^{-\lambda(T_{TRAN} + T_{CHEM} + T_{QC})}, \ \forall \, t \in T, \tag{21}$$

wherein $Q_t^{EOU}$ is the total amount of radionuclides produced at the end of target unloading process of the one or more cyclotrons in production stage t, wherein FR is a percentage of the radionuclides lost due to radioactive decay during the target unloading process of the one or more cyclotrons in production stage t, wherein PY is the percent yield of the radionuclides through the target unloading process of the one or more cyclotrons in production stage t, wherein QS is a percentage of the radionuclides at end of the chemistry process of the one or more cyclotrons in production stage t, wherein $T_{TRAN}$ is the amount of time required for completing the radionuclide transfer process of the one or more cyclotrons in production stage t, wherein $T_{CHEM}$ is the time required for the chemistry process of the one or more cyclotrons in production stage t, and wherein $T_{QC}$ is the time required for the quality control process of the one or more cyclotrons in production stage t;

wherein $Q_t^{EOU}$ is determined by solving the following expression (20):

$$Q_t^{EOU} = \left[\sum_{i\in C}\sum_{j\in G} BC_{ijt} * SY_{ij} * EN_{ij} * \left(1 - e^{\lambda(EOB_{ijt} - BOB_{ijt})}\right)\right] * e^{-\lambda(EOU_t - EOB_{ijt})}, \forall\, t \in T, \quad (20)$$

wherein T={1, . . . , $N_{PRD}$}, where $N_{PRD}$ is the number of production stages considered, wherein C={1, . . . , $N_{CYCL}$}, where $N_{CYCL}$ is the number of cyclotrons available in the production facility, wherein G={1, . . . , $N_{TRG}$}, where $N_{TRG}$ is the number of targets available in all cyclotrons that exist in the production facility, wherein $BC_{ijt}$ is the beam current of cyclotron i, target j, in production stage t, wherein $SY_{ij}$ is the saturation yield of cyclotron i and target j, wherein $EN_{ij}$ is the enrichment of the radionuclide precursor in cyclotron i and target j, wherein $EOB_{ijt}$ is the time at end of bombardment of cyclotron i, target j, in production stage t, wherein $BOB_{ijt}$ is the time at beginning of bombardment of cyclotron i, target j, in production stage t, and wherein $EOU_t$ is the time at end of all target unloading process in production stage t;

wherein ($EOB_{ijt}$–$BOB_{ijt}$), the duration of bombardment of cyclotron i, target j, in production stage t, is minimized by the following expression (13):

$$\min \sum_{i\in C}\sum_{j\in G}\sum_{t\in T} ((EOB_{ijt} - BOB_{ijt})t, \quad (13)$$

subject to the following constraints (14) through (19), $$T_{BMB}^{min} * z_{ijt} \le EOB_{ijt} - BOB_{ijt} \le T_{BMB}^{max} * z_{ijt}, \forall i \in C, \forall j \in G, \forall t \in T, \quad (14)$$

wherein $T_{BMB}^{min}$ is minimum bombardment time, $T_{BMB}^{max}$ is maximum bombardment time, $$BC^{min} * z_{ijt} \le BC_{ijt} \le BC^{max} * z_{ijt}, \forall i \in C, \forall j \in G, \forall t \in T, \quad (15)$$

wherein $BC^{min}$ and $BC^{max}$ are the lower and upper bounds of beam current used for the cyclotron i, respectively, and $BC_{ijt}$ is the beam current of cyclotron i, target j, in production stage t, $$EOB_{i1t} = EOB_{ijt}, \forall i \in C, \forall j \in G, \forall t \in T, \quad (16)$$

wherein $EOB_{i1t}$ is the time of the end of bombardment of cyclotron i, target 1, in production stage t; wherein constraint (16) provides that for every cyclotron, the end of the bombardment of all of the targets happen at the same time, $$EOB_{i1t} + \sum_{j\in G} z_{ijt} * T_{ij}^{UNLD} \le EOU_t, \forall\, i \in C, \forall\, t \in T, \quad (17)$$

wherein $T_{ij}^{UNLD}$ is the unload time of target j in cyclotron i, and $EOU_t$ is the latest time of completion of all unloading process in production stage t, wherein constraint (17) provides that at every production stage t, each target j in cyclotron i is unloaded sequentially after the end of the bombardment process, $$BOB_{ij1} = T_{INIT}\ \forall i \in C, \forall j \in G, \quad (18)$$

wherein $T_{INIT} = T_{START} + T_{CYCL\text{-}INIT} + T_{TRG\text{-}LOAD} + T_{TUNE\text{-}BEAM}$, wherein $BOB_{ij1}$ defines the time of the beginning of bombardment of cyclotron i, target j, in production stage 1, $T_{INIT}$ represents the total amount of time required before the bombardment begins, $T_{START}$ represents the time when the production process starts where the time is in minutes past midnight, $T_{CYCL\text{-}INIT}$ is amount of time required to initialize cyclotron i, $T_{TRG\text{-}LOAD}$ is amount of time required to load target j, and $T_{TUNE\text{-}BEAM}$ is amount of time required to tune cyclotron i's beam current; and $$BOB_{ijt} \ge EOU_{t-1}(+T_{PREP}), \forall i \in C, \forall j \in G, \forall t T - \{1\}, \quad (19)$$

wherein $EOU_{t-1}$ is the time point representing the end of unloading of target j in production stage t−1, and $T_{PREP}$ is the amount of time required to prepare cyclotron i for next production stage, where constraint (19) provides that the beginning of the bombardment in production stage t must happen after the dispensing process in the previous stage t-1.

2. The method of claim 1, wherein $T_{BMB}^{min}$=30 minutes and $T_{BMB}^{max}$=4 hours or 240 minutes.

3. The method of claim 1, wherein $BC^{min}$=40 μA and $BC^{max}$=80 μA.

4. A method for producing an optimized amount of radiopharmaceutical for preparation of doses for use in nuclear imaging at customer sites in order to meet aggregate demands of orders placed by the customer sites, wherein the radiopharmaceutical is produced at a production facility operating one or more cyclotrons, wherein the production of radiopharmaceutical comprises: a cyclotron bombardment process stage during which a target radionuclide precursor material is bombarded with charged particles to produce a radionuclide material; a target unload process stage; a radionuclide transfer process stage during which the radionuclide material is transferred from the target unload process stage to a chemistry process stage, wherein during the chemistry process stage the radionuclide material is converted in to a radiopharmaceutical; a quality control process stage during which the radiopharmaceutical is sampled for quality control testing; a dose dispensing process stage during which the radiopharmaceutical is dispensed into individual doses for delivery to the customer sites, the method comprising:

using a computer, determining the total amount of radionuclide $Q_t^{DSP}$ that is desired to be produced by $N_{CYCL}$ number of cyclotrons and $N_{TRG}$ number of targets in the production facility at the end of dose dispensing process in production stage t, (where t=1 to $N_{PRD}$), wherein $Q_t^{DSP}$ is sufficient to meet the aggregate amount of radiopharmaceuticals $Q^{CUST}$ ordered by the customer sites while minimizing any overproduction of the radionuclide, whereby $Q_t^{DSP}$ meets the following conditional constraint (23):

$$Q_t^{DSP} \geq \sigma \sum_{i \in H_t} q_i * e^{-\lambda(T_{it}^{INJ} - T_t^{DSP})}, \forall t \in T \quad (23)$$

wherein $\sigma$ is $\geq 1$, $q_i$ is the total radioactivity demand of customer site i that has placed one or more orders, wherein $H_t = \{2, \ldots, N_{SITES}\}$, where $N_{SITES}$ is the number of customer sites that have placed orders whose demand is to be satisfied by production stage t, wherein $\lambda$ is the radioactivity decay rate of the radionuclide, wherein $T_{it}^{INJ}$ is the time for the earliest order for radiopharmaceutical among the one or more orders placed by customer site i whose demand is to be satisfied by production stage t, wherein $T_t^{DSP}$ is the time when the dose dispensing process begins in production stage t, and is defined by the following expression (22):

$$T_t^{DSP} = EOU_t = T_{TRAN} + T_{CHEM} + T_{QC}, \forall t \in T, \quad (22)$$

wherein the $Q_t^{DSP}$ is determined by solving the following expression (21):

$$Q_t^{DSP} = Q_t^{EOU} * (1 - FR) * PY * (1 - QS) * e^{-\lambda(T_{TRAN} + T_{CHEM} + T_{QC})}, \quad \forall t \in T, \quad (21)$$

wherein $Q_t^{EOU}$ is the total amount of radionuclides produced at the end of target unloading process of the one or more cyclotrons in production stage t, wherein FR is the percentage of the radionuclides lost due to radioactive decay during the target unloading process of the one or more cyclotrons in production stage t, wherein PY is the percent yield of the radionuclides through the target unloading process of the one or more cyclotrons in production stage t, wherein QS is a percentage of the radionuclides at end of the chemistry process of the one or more cyclotrons in production stage t, wherein $T_{TRAN}$ is the amount of time required for completing the radionuclide transfer process of the one or more cyclotrons in production stage t, wherein $T_{CHEM}$ is the time required for the chemistry process of the one or more cyclotrons in production stage t, and wherein $T_{QC}$ is the time required for the quality control process of the one or more cyclotrons in production stage t;

wherein $Q_t^{EOU}$ is determined by solving the following expression (20):

$$Q_t^{EOU} = \left[\sum_{i \in C} \sum_{j \in G} BC_{ijt} * SY_{ij} * EN_{ij} * \left(1 - e^{\lambda(EOB_{ijt} - BOB_{ijt})}\right)\right] * e^{-\lambda(EOU_t - EOB_{ijt})}, \forall t \in T, \quad (20)$$

wherein $T = \{1, \ldots, N_{PRD}\}$, where $N_{PRD}$ is the number of production stages considered, wherein $C = \{1, \ldots, N_{CYCL}\}$, where $N_{CYCL}$ is the number of cyclotrons available in the production facility, wherein $G = \{1, \ldots, N_{TRG}\}$, where $N_{TRG}$ is the number of targets available in all cyclotrons that exist in the production facility, wherein $BC_{ijt}$ is the beam current of cyclotron i, target j, in production stage t, wherein $SY_{ij}$ is the saturation yield of cyclotron i and target j, wherein $EN_{ij}$ is the enrichment of the radionuclide precursor in cyclotron i and target j, wherein $EOB_{ijt}$ is the time at end of bombardment of cyclotron i, target j, in production stage t, wherein $BOB_{ijt}$ is the time at beginning of bombardment of cyclotron i, target j, in production stage t, and wherein $EOU_t$ is the time at end of all target unloading process in production stage t;

wherein $(EOB_{ijt} - BOB_{ijt})$, the duration of bombardment of cyclotron i, target j, in production stage t, is minimized by the following expression (13):

$$\min \sum_{i \in C} \sum_{j \in G} \sum_{t \in T} ((EOB_{ijt} - BOB_{ijt})t, \quad (13)$$

subject to the following constraints (14) through (19), $$T_{BMB}^{min} * z_{ijt} \leq EOB_{ijt} - BOB_{ijt} \leq T_{BMB}^{max} * z_{ijt}, \forall i \in C, \forall j \in G, \forall t \in T, \quad (14)$$

wherein $T_{BMB}^{min}$ is the minimum bombardment time, $T_{BMB}^{max}$ is the maximum bombardment time, $$BC^{min} z *_{ijt} \leq BC_{ijt} \leq BC^{max} * z_{ijt}, \forall i \in C, \forall j \in G, \forall t \in T, \quad (15)$$

wherein $BC^{min}$ and $BC^{max}$ are the lower and upper bounds of beam current used for the cyclotron i, respectively, and $BC_{ijt}$ is the beam current of cyclotron i, target j, in production stage t, $$EOB_{i1t} = EOB_{ijt}, \forall i \in C, \forall j \in G, \forall t \in T, \quad (16)$$

wherein $EOB_{i1t}$ is the time of the end of bombardment of cyclotron i, target 1, in production stage t; wherein the constraint (16) provides that for every cyclotron, the end of the bombardment of all of the targets happen at the same time, $$EOB_{i1t} + \sum_{j \in G} z_{ijt} * T_{ij}^{UNLD} \leq EOU_t, \forall i \in C, \forall t \in T, \quad (17)$$

is the unload time of target j in cyclotron i, and $EOU_t$ is the latest time of completion of all unloading process in production stage t, wherein the constraint (17) provides that at every production stage t, each target j in cyclotron i is unloaded sequentially after the end of the bombardment process, $$BOB_{tj1} = T_{INIT} \forall i \in C, \forall j \in G, \quad (18)$$

wherein $T_{INIT} = T_{START} + T_{CYCL\text{-}INIT} + T_{TRG\text{-}LOAD} + T_{TUNE\text{-}BEAM}$, wherein $BOB_{y1}$ defines the time of the beginning of bombardment of cyclotron i, target j, in production stage 1, $T_{INIT}$ represents the total amount of time required before the bombardment begins, $T_{START}$ represents the time when the production process starts where the time is in minutes past midnight, $T_{CYCL\text{-}INIT}$ is amount of time required to initialize cyclotron i, $T_{TRG\text{-}LOAD}$ is amount of time required to load target j, and $T_{TUNE\text{-}BEAM}$ is amount of time required to tune cyclotron i's beam current; and $$BOB_{ijt} \geq EOU_{t-1}(+T_{PREP}), \forall i \in C, \forall j \in G, \forall t T - \{1\}, \quad (19)$$

wherein $EOU_{t-1}$ is the time point representing the end of unloading of target j in production stage t-1, and $T_{PREP}$ is the amount of time required to prepare cyclotron i for next production stage, where constraint (19) provides that the beginning of the bombardment in production stage t must happen after the dispensing process in the previous stage t-1; and operating each of the cyclotron i with target j in a production stage t so that the cyclotron's bombardment process begins at time BOBijt and ends at time EOBijt to produce an appropriate amount of radionuclide to produce the determined amount of $Q_t^{DSP}$ of radiopharmaceutical at the end of dose dispensing process according to the constraints (14)-(19).

5. The method of claim 4, wherein $T_{BMB}^{min}$=30 minutes and $T_{BMB}^{max}$=4 hours or 240 minutes.

6. The method of claim 4, wherein $BC^{min}$=40 µA and $BC^{max}$=80 µA.

7. A control system for controlling the operation of a radiopharmaceutical production facility, the radiopharmaceutical being for use in nuclear imaging at customer sites, in order to meet aggregate demands of orders placed by the customer sites, wherein the production facility is operating one or more cyclotrons, wherein the production of radiopharmaceutical comprises: a cyclotron bombardment process stage during which a target radionuclide precursor material is bombarded with charged particles to produce a radionuclide material; a target unload process stage; a radionuclide transfer process stage during which the radionuclide material is transferred from the target unload process stage to a chemistry process stage, wherein during the chemistry process stage the radionuclide material is converted in to a radiopharmaceutical; a quality control process stage during which the radiopharmaceutical is sampled for quality control testing; a dose dispensing process stage during which the radiopharmaceutical is dispensed into individual doses for delivery to the customer sites, the control system comprising:

a processor having a non-transitory machine-readable storage medium encoded with computer program code, wherein when the processor executes the computer program code, the processor performs a method comprising the steps of:

determining the total amount of radionuclide $Q_t^{DSP}$ that is desired to be produced by $N_{CYCL}$ number of cyclotrons and $N_{TRG}$ number of targets in the production facility at the end of dose dispensing process in production stage t, (where t=1 to $N_{PRD}$), wherein $Q_t^{DSP}$ is sufficient to meet the aggregate amount of radiopharmaceuticals $Q^{CUST}$ ordered by the customer sites while minimizing any overproduction of the radionuclide, whereby $Q_i^{DSP}$ meets the following conditional constraint (23):

$$Q_t^{DSP} \geq \sigma \sum_{i \in H_t} q_i * e^{-\lambda(T_{it}^{INJ} - T_t^{DSP})}, \forall\, t \in T \tag{23}$$

wherein σ is ≥1, $q_i$ is the total radioactivity demand of customer site i that has placed one or more orders, wherein $H_t$={2, . . . , $N_{SITES}$}, where $N_{SITES}$ is the number of customer sites that have placed orders whose demand is to be satisfied by production stage t, wherein λ is the radioactivity decay rate of the radionuclide, wherein $T_{it}^{INJ}$ is the time for the earliest order for radiopharmaceutical among the one or more orders placed by customer site i whose demand is to be satisfied by production stage t, wherein $T_t^{DSP}$ is the time when the dose dispensing process begins in production stage t, and is defined by the following expression (22):

$$T_t^{DSP} = EOU_t + T_{TRAN} + T_{CHEM} + T_{OC},\ \forall t \in T, \tag{22}$$

wherein the $Q_t^{DSP}$ is determined by solving the following expression (21):

$$Q_t^{DSP} = Q_t^{EOU} * (1 - FR) * PY * (1 - QS) * e^{-\lambda(T_{TRAN} + T_{CHEM} + T_{QC})}, \quad \forall\, t \in T, \tag{21}$$

wherein $Q_t^{EOU}$ is the total amount of radionuclides produced at the end of target unloading process of the one or more cyclotrons in production stage t, wherein FR is the percentage of the radionuclides lost due to radioactive decay during the target unloading process of the one or more cyclotrons in production stage t, wherein PY is the percent yield of the radionuclides through the target unloading process of the one or more cyclotrons in production stage t, wherein QS is a percentage of the radionuclides at end of the chemistry process of the one or more cyclotrons in production stage t, wherein $T_{TRAN}$ is the amount of time required for completing the radionuclide transfer process of the one or more cyclotrons in production stage t, wherein $T_{CHEM}$ is the time required for the chemistry process of the one or more cyclotrons in production stage t, and wherein $T_{QC}$ is the time required for the quality control process of the one or more cyclotrons in production stage t;

wherein $Q_t^{EOU}$ is determined by solving the following expression (20):

$$Q_t^{EOU} = \left[\sum_{i \in C} \sum_{j \in G} BC_{ijt} * SY_{ij} * EN_{ij} * \left(1 - e^{\lambda(EOB_{ijt} - BOB_{ijt})}\right)\right] * e^{-\lambda(EOU_t - EOB_{ijt})}, \forall\, t \in T, \tag{20}$$

wherein T={1, . . . , $N_{PRD}$}, where $N_{PRD}$ is the number of production stages considered, wherein C={1, . . . , $N_{CYCL}$}, where $N_{CYCL}$ is the number of cyclotrons available in the production facility, wherein G={1, . . . , $N_{TRG}$}, where $N_{TRG}$ is the number of targets available in all cyclotrons that exist in the production facility, wherein $BC_{ijt}$ is the beam current of cyclotron i, target j, in production stage t, wherein $SY_{ij}$ is the saturation yield of cyclotron i and target j, wherein $EN_{ij}$ is the enrichment of the radionuclide precursor in cyclotron i and target j, wherein $EOB_{ijt}$ is the time at end of bombardment of cyclotron i, target j, in production stage t, wherein $BOB_{ijt}$ is the time at beginning of bombardment of cyclotron i, target j, in production stage t, and wherein $EOU_t$ is the time at end of all target unloading process in production stage t;

wherein $(EOB_{ijt}-BOB_{ijt})$, the duration of bombardment of cyclotron i, target j, in production stage t, is minimized by the following expression (13):

$$\min\sum_{i\in C}\sum_{j\in G}\sum_{t\in T}((EOB_{ijt}-BOB_{ijt})t, \quad (13)$$

subject to the following constraints (14) through (19), $$T_{BMB}^{min}*z_{ijt}\leq EOB_{ijt}-BOB_{ijt}\leq T_{BMB}^{max}*z_{ijt},\ \forall i\in C,\ \forall j\in G,\ \forall t\in T, \quad (14)$$

wherein $T_{BMB}^{min}$ is minimum bombardment time, $T_{BMB}^{max}$ is maximum bombardment time, $$BC^{min}*z_{ijt}\leq BC_{ijt}\leq BC^{max}*z_{ijt},\ \forall i\in C,\ \forall j\in G,\ \forall t\in T, \quad (15)$$

wherein $BC^{min}$ and $BC^{max}$ are the lower and upper bounds of beam current used for the cyclotron i, respectively, and $BC_{ijt}$ is the beam current of cyclotron i, target j, in production stage t, $$EOB_{i1t}=EOB_{ijt},\ \forall i\in C,\ \forall j\in G,\ \forall t\in T, \quad (16)$$

wherein $EOB_{i1t}$ is the time of the end of bombardment of cyclotron i, target 1, in production stage t; wherein constraint (16) provides that for every cyclotron, the end of the bombardment of all of the targets happen at the same time, $$EOB_{i1t}+\sum_{j\in G}z_{ijt}*T_{ij}^{UNLD}\leq EOU_t,\ \forall\ i\in C,\ \forall\ t\in T,\ \text{wherein } T_{ij}^{UNLD} \quad (17)$$

wherein $T_{ij}^{UNLD}$ is the unload time of target j in cyclotron i, and $EOU_t$ is the latest time of completion of all unloading process in production stage t, wherein constraint (17) provides that at every production stage t, each target j in cyclotron i is unloaded sequentially after the end of the bombardment process, $$BOB_{ij1}=T_{INIT}\ \forall i\in C,\ \forall j\in G, \quad (18)$$

wherein $T_{INIT}=T_{START}+T_{CYCL\text{-}INIT}+T_{TRG\text{-}LOAD}$ $T_{TUNE\text{-}BEAM}$, wherein $BOB_{y1}$ defines the time of the beginning of bombardment of cyclotron i, target j, in production stage 1, $T_{INIT}$ represents the total amount of time required before the bombardment begins, $T_{START}$ represents the time when the production process starts where the time is in minutes past midnight, $T_{CYCL\text{-}INIT}$ is amount of time required to initialize cyclotron i, $T_{TRG\text{-}LOAD}$ is amount of time required to load target j, and $T_{TUNE\text{-}BEAM}$ is amount of time required to tune cyclotron i's beam current; and $$BOB_{ijt}\geq EOU_{t-1}(+T_{PREP}),\ \forall i\in C,\ \forall j\in G,\ \forall t T-\{1\}, \quad (19)$$

wherein $EOU_{t-1}$ is time point representing the end of unloading of target j in production stage t-1, and $T_{PREP}$ is amount of time required to prepare cyclotron i for next production stage, where constraint (19) provides that the beginning of the bombardment in production stage t must happen after the dispensing process in the previous stage t−1.

8. The method of claim 7, wherein $T_{BMB}^{min}$=30 minutes and $T_{BMB}^{max}$=4 hours or 240 minutes.

9. The method of claim 7, wherein $BC^{min}$=40 μA and $BC^{max}$=λμA.

* * * * *